(12) United States Patent
Hemmingsson et al.

(10) Patent No.: US 8,539,809 B2
(45) Date of Patent: Sep. 24, 2013

(54) METHOD AND DEVICE FOR TESTING THE MEASURING FUNCTION OF A MEASURING DEVICE

(75) Inventors: Tryggve Hemmingsson, Sollentuna (SE); Mats Carlsson, Täby (SE)

(73) Assignee: Aerocrine AB, Solna (SE)

( * ) Notice: Subject to any disclaimer, the term of this patent is extended or adjusted under 35 U.S.C. 154(b) by 546 days.

(21) Appl. No.: 12/525,301

(22) PCT Filed: Jan. 28, 2008

(86) PCT No.: PCT/SE2008/050104
§ 371 (c)(1),
(2), (4) Date: Nov. 12, 2009

(87) PCT Pub. No.: WO2008/094118
PCT Pub. Date: Aug. 7, 2008

(65) Prior Publication Data
US 2010/0089121 A1     Apr. 15, 2010

(30) Foreign Application Priority Data

Jan. 30, 2007   (SE) ...................................... 0700227

(51) Int. Cl.
*G01N 21/00*        (2006.01)
(52) U.S. Cl.
USPC ......................................................... 73/1.06
(58) Field of Classification Search
USPC .................................................. 73/1.06, 23.3
See application file for complete search history.

(56) References Cited

U.S. PATENT DOCUMENTS

| | | | |
|---|---|---|---|
| 4,323,064 A | 4/1982 | Hoenig et al. | 128/204.21 |
| 5,421,189 A | 6/1995 | Dussault | 73/19.1 |
| 5,635,620 A | 6/1997 | Ronge et al. | 73/1.05 |
| 5,770,793 A | 6/1998 | Stock | 73/23.21 |
| 6,960,290 B2 * | 11/2005 | Akhavan et al. | 205/783 |

(Continued)

FOREIGN PATENT DOCUMENTS

WO     2004/059317 A1     7/2004

OTHER PUBLICATIONS

International Preliminary Report on Patent Patentability completed Feb. 3, 2009, for PCT Application No. PCT/SE2008/050104 filed Jan. 28, 2008, 5 pages.

(Continued)

*Primary Examiner* — Peter J Macchiarolo
*Assistant Examiner* — Tamiko Bellamy
(74) *Attorney, Agent, or Firm* — Renner, Otto, Boisselle & Sklar, LLP

(57) ABSTRACT

The present invention relates to the field of gas measurements, and more specifically to the field of testing the measuring function of a measuring device (7) for gas measurements, the measuring device (7) including a gas sensor (9) generating at least one output signal. The method includes connecting at least one simulation signal to the measuring device (7) and/or feeding a gas mixture to the measuring device wherein the magnitude of the concentration of a gas to be measured in the gas mixture is known. The invention also relates to a simulation device (1) for connection to the measuring device (7) for gas measurements when testing the measuring function of the measuring device (7). The simulation device (1) generates at least one simulation signal which can attain at least one signal level, wherein a certain signal value corresponds to a certain gas concentration.

11 Claims, 5 Drawing Sheets

(56) References Cited

U.S. PATENT DOCUMENTS

| | | | |
|---|---|---|---|
| 7,014,692 B2 | 3/2006 | Nilsson et al. | 96/135 |
| 7,260,976 B2 | 8/2007 | Colman et al. | 73/1.06 |
| 7,413,645 B2 | 8/2008 | Scheffler | 205/775 |
| 2001/0018844 A1 | 9/2001 | Parekh | 73/1.06 |
| 2003/0136176 A1 | 7/2003 | Ruiz | 73/23.2 |
| 2004/0017570 A1 | 1/2004 | Parikh et al. | 356/437 |
| 2006/0000256 A1 | 1/2006 | Orr et al. | 73/1.16 |
| 2006/0263254 A1 | 11/2006 | Lee | 73/23.21 |

OTHER PUBLICATIONS

International Search Report mailed Apr. 9, 2008, for PCT Application No. PCT/SE2008/050104 filed Jan. 28, 2008, 5 pages.

International Written Opinion mailed Apr. 9, 2008, for PCT Application No. PCT/SE2008/050104 filed Jan. 28, 2008, 6 pages.

Non Final Office Action received for U.S. Appl. No. 12/525,306, mailed on Mar. 16, 2012, 11 pages.

International Search Report received for PCT Patent Application No. PCT/SE2008/050105, mailed Jun. 2, 2008, 4 pages.

\* cited by examiner

METHOD AND DEVICE FOR TESTING THE MEASURING FUNCTION OF A MEASURING DEVICE

CROSS REFERENCE TO RELATED APPLICATIONS

This application is a U.S. National Phase patent application of International Application No. PCT/SE2008/050104, with an international filing date of Jan. 28, 2008, which claims priority to Sweden Patent Application No. 0700227-2, filed on Jan. 30, 2007, all of which are incorporated herein by reference in their entirety.

TECHNICAL FIELD

The present invention relates to the field of gas measurements, and more specifically to the field of testing the measuring function of a measuring device for gas measurements, the measuring device including a gas sensor generating at least one output signal.

The present invention also relates to a simulation device.

BACKGROUND OF THE INVENTION

For testing the measuring function of a measuring device for gas measurements it is known to use a special reference gas with a known concentration of the gas to be measured by the measuring device. For example, if the measuring device is used to measure the concentration of nitrogen monoxide in exhaled breath, a special reference gas with a known concentration of nitrogen monoxide in nitrogen is used. That is, the bulk gas is nitrogen which contains a specified concentration of nitrogen monoxide. This special reference gas is stored in compressed form in a gas cylinder and is then fed to the measuring device, often via a pressure regulator and a gas fitting. The reading of the measuring device is then compared with the known concentration of the gas to be measured in the special reference gas. One type of pressure regulator comprises 2 pressure meters, a valve for manually adjusting the output pressure of the regulator and a stop valve at the output of the regulator.

This technique is expensive because of the cost of the special reference gas. In some cases it is also difficult to manufacture the special reference gas within the required specifications. This is for example the case when a special reference gas with a low concentration of the gas to be measured is needed. It is also time consuming to acquire the special reference gas and the handling of the gas cylinder is inconvenient because of the size and weight of the gas cylinder.

A measuring device for gas measurements can functionally be seen as comprising two parts. A first part (gas processing part) that processes the gas to be measured, including a gas sensor giving at least one electrical output value, and a second part (measurement value processing part) that processes and displays or outputs the at least one output value from the gas processing part.

SUMMARY OF THE INVENTION

One aim of the present invention is to provide a technique that leads to improvements in comparison to the known technique for example in terms of costs, simplified handling, reliability, accuracy and control of accuracy.

This aim is achieved by the method according to independent claim 1 and further by the device according to independent claim 11.

The term signal used in this application is meant to be understood as an electrical signal.

This application relates to the measurement of a gas present in a gas mixture. The gas which is the subject of the measurement is called "the gas to be measured" or "analyte". For example the concentration in the gas mixture of the gas to be measured can be measured. The two expressions "analyte" and "the gas to be measured" are both used, they are intended to have substantially the same meaning.

One advantage of the present invention is that no special reference gas from a gas cylinder is necessary. For example, this makes the testing or checking process simpler in so far that no special reference gas has to be acquired, and it reduces the cost. Furthermore, the testing or checking process becomes less cumbersome since no gas cylinder is needed, to handle a pressurised gas cylinder can be unpleasant and too technical for many persons handling a measuring device for gas measurements. The pressure of a full gas cylinder can for example be very high, typically 170 Bar. This can be experienced as uncomfortable and dangerous to handle for many persons handling a measuring device for gas measurements. Moreover, the handling becomes easier since no gas cylinder is needed, such a gas cylinder can not be transported in an easy way.

According to the solution of the invention as defined in independent claim 1 there is provided a method for testing or checking the measuring function of a measuring device, where the measuring device is used for gas measurements.

In this method, a scrubber or filter having an input and an output connection end, is connected with its output connection end to a gas inlet opening of the measuring device. The scrubber or filter filters out or substantially filters out the gas to be measured.

The input connection end of the scrubber or filter is then supplied with exhaled breath. Hence, the measuring device is supplied with exhaled breath substantially free from the gas to be measured via the scrubber or filter. The exhaled breath is then processed by the measuring device, the measuring device giving a reading or displaying a measured value of the measured concentration of the gas to be measured in the exhaled breath supplied to the measuring device.

The reading or the displayed measurement value of the measuring device is then compared with, and/or evaluated in relation to, the known magnitude of the concentration of the gas to be measured in the exhaled breath supplied to the measuring device.

One advantage of the use of the scrubber or filter is that the complete measuring function of the measuring device can be tested without the need of using a special reference gas.

Another advantage is that the measuring accuracy of the measuring device can be tested since the scrubber or filter has an ensured maximum level of the rest concentration of the gas to be measured in the gas mixture, e.g. exhaled breath, at the output from the scrubber or filter. This maximum rest concentration amounts to less than around 5 ppb (parts per billion) for certain NO-scrubbers or NO-filters. Some measuring devices of the type described in this application have a zero level defined as a concentration of less than around 5 ppb. When applying the testing or checking method according to this invention of course the scrubber or filter used has to be adapted to the measuring device in question and to the definition of the zero level of that measuring device.

Hence, it can be tested that the measuring device gives or indicates a zero reading when a gas mixture with zero concentration (within the defined tolerance for a zero level) of the gas to be measured is fed to the measuring device.

Yet another advantage is that the measuring accuracy of the measuring device can be tested for a zero concentration (within the defined tolerance for a zero level) of the gas to be measured. This is a particular advantage since it is often a problem to obtain a good measuring accuracy for very low or zero concentrations of the gas to be measured.

In a preferred embodiment of the method according to the invention, the measuring device includes or comprises among other things a gas sensor that generates at least one output signal, and the method includes or comprises a first step of connecting or feeding at least one simulation signal with a known signal value to the measuring device.

In a second step the reading of the measuring device, or the measured value displayed by the measuring device, is compared with, and/or evaluated in relation to, the known signal value of the at least one simulation signal.

An advantage of the above described method is that no special reference gas is needed. Another advantage is that the measuring function and the measuring accuracy of the measurement value processing part of the measuring device can be tested separately, independent of the gas processing part.

In another preferred embodiment of the method according to the invention, the method further includes or comprises the step of simulating or modelling the at least one output signal from the gas sensor, by generating at least one simulation signal, which is simulating the at least one output signal from the gas sensor. The at least one simulation signal can attain at least one signal level. Moreover, the at least one simulation signal, which can attain at least one signal level, is fed or connected to the measuring device.

An advantage of this embodiment is among other things that the measuring device can be fed with at least one signal simulating the at least one output signal from the gas sensor. Hence, the output of the gas sensor can be simulated and since the at least one simulation signal can attain at least one signal level, the measuring function of the measuring device can be tested for at least one gas concentration.

Another preferred embodiment of the method according to the invention includes the disconnection of the gas sensor from the measuring device and the connection of a simulation device to the measuring device. The simulation device generates the at least one simulation signal, which can attain at least one signal level.

This embodiment offers among other things a convenient way of feeding the at least one simulation signal to the measuring device.

Another preferred embodiment of the method according to the invention includes setting or adjusting the at least one simulation signal of the simulation device to at least one of a plurality of signal levels.

This embodiment offers among other things a convenient way of testing the measuring device with different signal levels. A certain signal value or signal level corresponds to a certain concentration of the gas to be measured.

In another preferred embodiment of the method according to the invention, the scrubber or filter is a scrubber or filter for nitrogen monoxide (NO-scrubber or NO-filter) and the gas to be measured is nitrogen monoxide.

This brings the further advantage that the measuring function and measuring accuracy of the measuring device can be tested or checked for a very low or zero concentration of nitrogen monoxide.

Preferably an input filter, for filtering out moist, virus, microbes, bacteria and the like is used together with the scrubber or filter. The input filter has an input and an output connection end and is connected with its output connection end to the input connection end of the scrubber or filter. Further, exhaled breath is supplied to the input connection end of the input filter.

Hence, the measuring device is supplied with exhaled breath via the input filter and the scrubber or filter. When the exhaled breath reaches the measuring device the exhaled breath is substantially free from the gas to be measured, and substantially free from moist, virus, microbes, bacteria and the like. The exhaled breath is then processed by the measuring device, the measuring device giving a reading, or displaying a measurement value, of the measured concentration of the gas to be measured.

The reading or the displayed measurement value of the measuring device is then compared with, and/or evaluated in relation to, the known magnitude of the concentration of the gas to be measured in the exhaled breath supplied to the measuring device.

An advantage of the use of the input filter is that moist, virus, microbes, bacteria and the like are prevented from entering the measuring device with the exhaled breath of the human. Moist, virus, microbes, bacteria and the like can have an adverse effect on the functioning of the measuring device, and hence an adverse effect on the process of checking or testing the measuring function of the measuring device. Moreover, it is prevented that virus, microbes, bacteria and the like spread from one human to another via the measuring device.

In another preferred embodiment of the invention human exhalation is used. A human supply exhaled breath to a gas inlet opening of the measuring device.

This exhaled breath is then processed by the measuring device, the measuring device giving a reading, or displaying a measurement value, of the measured concentration of the gas to be measured in the exhaled breath supplied to the measuring device.

The reading or the displayed measurement value of the measuring device is then compared with, and/or evaluated in relation to, the known magnitude of the concentration of the gas to be measured in the exhaled breath supplied to the measuring device.

An advantage of this part of the method is that it can be tested that the measuring device gives a reading or displays a measurement value of a magnitude that is generally within the interval defined by the maximum and minimum values for the concentration of the gas to be measured in human exhaled breath. This part of the method is also an easy and convenient way of testing the measuring function of the measuring device.

In yet another preferred embodiment of the method according to the invention, an input filter, for filtering out moist, virus, microbes, bacteria and the like, having an input and an output connection end, is connected with its output connection end to a gas inlet opening of the measuring device.

After the input filter has been connected to the measuring device the human then supplies exhaled breath to the input filter by exhaling through the input connection end of the input filter.

The method steps as in the previously described embodiment are then executed. That is, processing of the exhaled breath by the measuring device and comparison and/or evaluation of the reading of the measuring device with/in relation to, the known magnitude of the concentration.

An advantage of the use of the input filter is that moist, virus, microbes, bacteria and the like are prevented from entering the measuring device with the exhaled breath of the human. Moist, virus, microbes, bacteria and the like can have an adverse effect on the functioning of the measuring device, and hence an adverse effect on the process of checking or testing the measuring function of the measuring device. Moreover, it is prevented that virus, microbes, bacteria and the like spread from one human to another via the measuring device.

In a further preferred embodiment of the invention the human inhales gas substantially free from, or with a reduced concentration of, the gas to be measured before supplying exhaled breath to the measuring device. After the human has inhaled gas substantially free from, or with a reduced concentration of, the gas to be measured, the human supply exhaled breath to the gas inlet opening of the measuring device or to the input connection end of the input filter.

This is an advantage in the case when the gas to be measured is present also in the ambient air. If the gas to be measured is present in the ambient air this can influence the concentration of the gas to be measured in the exhaled breath of the human. But by letting the human inhale a gas substantially free from, or with a reduced concentration of, the gas to be measured the influence of such a gas presence can be eliminated or at least almost eliminated, or reduced.

There are also synergistic effects provided by the combination of two or more parts of the method according to the invention. The different parts of the method according to the invention can be divided in three main categories:

i) The parts of the method relating to the use of the scrubber or filter.
ii) The parts of the method relating to the use of the simulation device generating the at least one simulation signal.
iii) The parts of the method relating to the use of human exhalation.

An advantage of combining one or more of the method parts from category i) with one or more of the method parts from category ii) and/or iii) is that the reliability of the test can be further increased.

With this combination of method parts the measuring function both of the measuring device as a whole, and of the measurement value processing part separately, can be tested. This makes it possible to detect a situation where there are errors both in the gas processing part and in the measurement value processing part, but of a type so that they even out each other.

That is, it can be the case that an error in the gas processing part influences the measuring function so as to give a reading that is too low, but an error in the measurement value processing part influences the measuring function so as to give a reading that is too high. In such a case, with a test method according to the prior art, where the measuring function of the measuring device as a whole is tested with a special reference gas, such errors might not be detected. On the other hand, by combining the appropriate parts of the method according to the invention, such errors can be detected.

According to the solution of the invention as defined in independent claim 11 there is provided a simulation device for connection to a measuring device for gas measurements when testing or checking the measuring function of the measuring device. The simulation device comprises generating means for generating at least one simulation signal. The simulation signal simulates or models at least one output signal of a gas sensor. The gas sensor is for or is used in a measuring device for gas measurements. The at least one simulation signal can attain at least one signal level, and a certain signal value or signal level corresponds to a certain gas concentration, the simulation device (1) having a specific sensitivity, and wherein the simulation device (1) has an identity detectable by the measuring device (7), enabling the sensitivity of the measuring device (7) to be set to the sensitivity of the simulation device (1).

The generating means may for example be electric or electronic circuitry.

One advantage of the simulation device is that the measurement value processing part can be tested independent from the other parts of the measuring device. Among other things this increases the reliability in testing the measuring function of the measuring device. Another advantage is the possibility of locating an error in the measuring device more specific. The error can be located to either the gas processing part or the measurement value processing part. Since the sensitivity of the measuring device 7 can be set to the sensitivity of the simulation device 1 by means of the identity of the simulation device 1, it is assured that the sensitivity of the measuring device 7 is correctly set in relation to the sensitivity of the simulation device 1.

According to another preferred embodiment of the simulation device of the invention, the simulation device comprises selection means such as a switch, a touch screen or a connector for receiving an external signal. The selection means is used for selecting at least one signal level of the at least one simulation signal.

This embodiment offers a convenient way of testing the measuring device with different signal levels.

BRIEF DESCRIPTION OF THE DRAWINGS

In the following the method and the device according to the invention will be described by way of example with reference to the accompanying drawings wherein.

DETAILED DESCRIPTION OF THE INVENTION

The method and the device according to the invention are applicable to any measuring device for gas measurements, where the measuring device has a gas sensor generating at least one output signal. One example is measuring devices for diagnostic gas measurements. However, in some of the examples described in the following, the method and the device according to the invention will be described in relation to a particular measuring device to facilitate the understanding of the invention. The measuring device in question is one model of the NIOX MINO®, marketed by Aerocrine AB, Solna, Sweden, which is used for diagnostic gas measurements.

Simulation Signal/Simulation Device

In the description below it will be referred to FIGS. 1, 2, 3 and 4.

Now a preferred embodiment of the method according to the invention will be described wherein a simulation device 1 described below is used together with a measuring device 7 for measuring for example the concentration of nitrogen monoxide in exhaled breath.

The simulation device 1 according to the invention generates at least one simulation signal that simulates at least one output signal of a gas sensor 9. The gas sensor 9 is used in a measuring device 7 for gas measurements. The generated at least one simulation signal can attain at least one signal level and has a known signal value.

Figure 3:
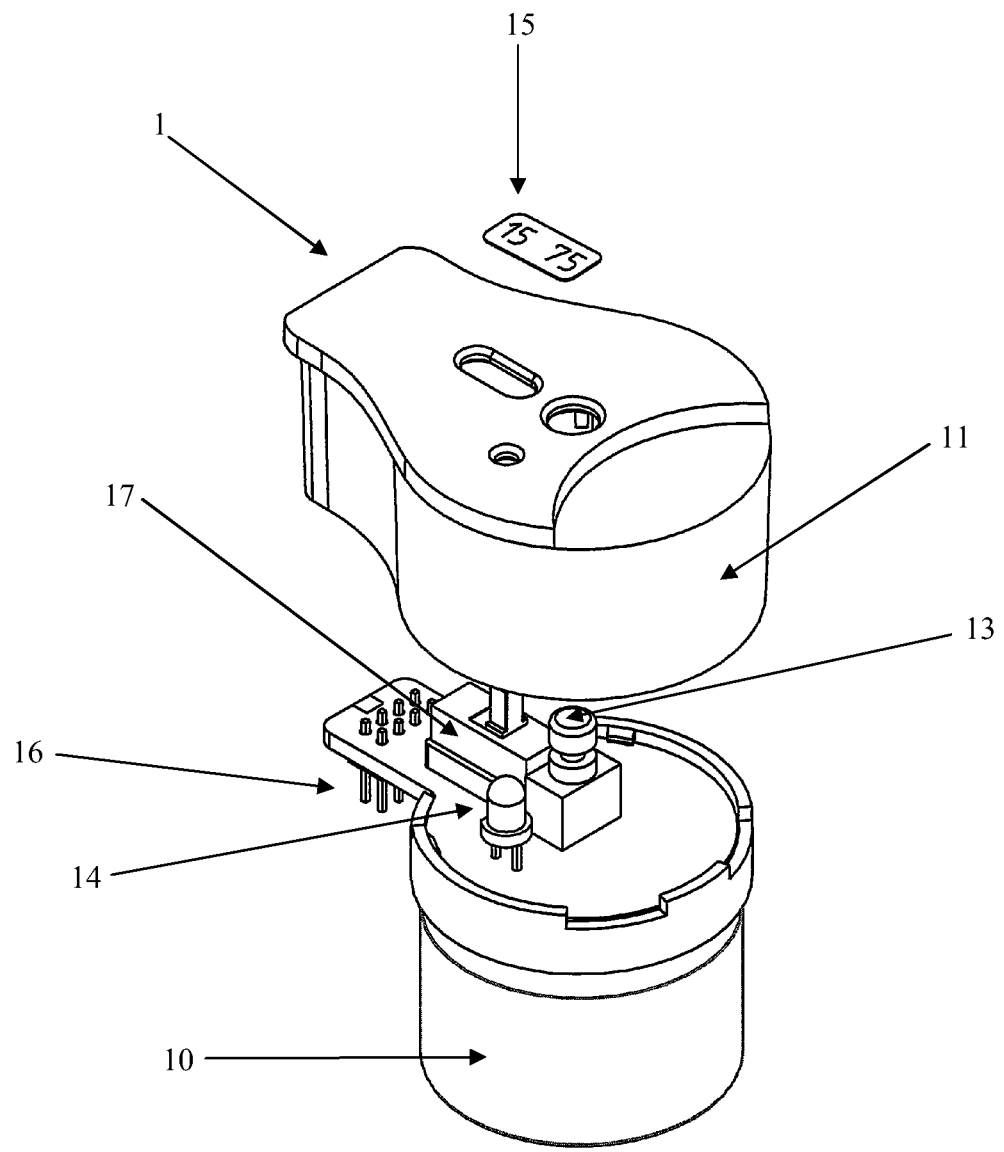
FIGS. 3 and 4 show a preferred embodiment of the simulation device 1 according to the invention.
Figure 4:
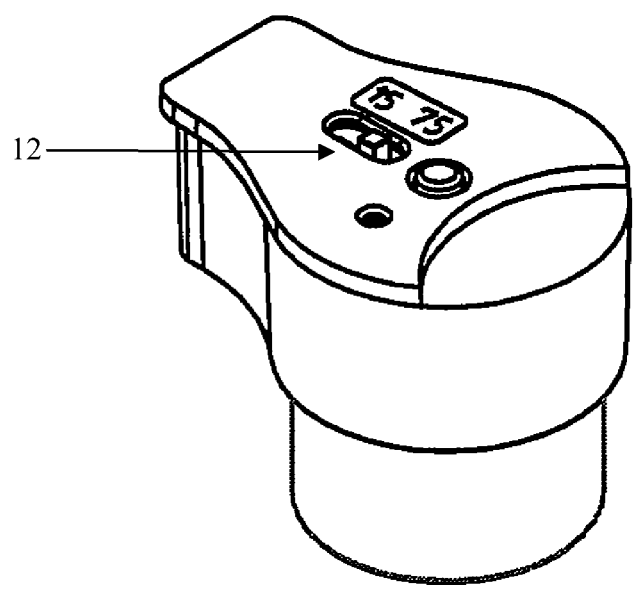

FIGS. 3 and 4 show a preferred embodiment of the simulation device 1 wherein the simulation device 1 comprises a housing 10, a housing cap 11, a selection device 12 in the form of a slide switch with two positions, a start button 13, an indicator 14, a scale or graduation 15, an electrical connector 16 and electric circuitry 17.

In this embodiment the simulation device 1 generates a simulation signal simulating the output signal of a gas sensor for measuring for example the concentration of nitrogen monoxide, such as the concentration of nitrogen monoxide in exhaled breath.

The simulation device 1 generates a simulation signal with two signal levels which correspond to or represent different concentrations of for example nitrogen monoxide.

It is conceivable with gas sensors having different sensitivities. The sensitivity expresses the relation between a certain electrical output value from a gas sensor 9 and the concentration of the gas to be measured, e.g. nitrogen monoxide. The sensitivity may e.g. be expressed in nanoampere (nA)/ppm or in millivolt (mV)/ppm (ppm stands for parts per million).

In the case that gas sensors having different sensitivities are used, the sensitivity of the measuring instrument 7 for the output signal from the gas sensor 9 has to be set to the sensitivity for the specific gas sensor 9 mounted in or connected to the measuring instrument 7. This may e.g. be done by the gas sensor 9 having an identity which is detected by the measuring instrument 7, and by which the sensitivity of the measuring instrument 7 can be set to the sensitivity of the gas sensor 9.

The selection device 12 is used to set the simulation signal to one of two levels, the levels corresponding to different concentrations of for example nitrogen monoxide, e.g. 15 ppb and 75 ppb.

The selection device 12 on the simulation device 1 is set to the level to be tested first, e.g. 15 ppb. The power supply is disconnected from the measuring device 7 and the gas sensor 9 is removed from the measuring device 7. The simulation device 1 is then inserted and electrically connected to the measuring device 7 where the gas sensor 9 was previously placed. The simulation device 1 can also be recognised by the measuring device 7 as the simulation device 1 is connected to the measuring device 7. See FIGS. 2B and 2C for an example showing the removal of a gas sensor 9 and the insertion of a simulation device 1 by one model of the measuring device 7 NIOX MINO®.

The simulation device 1 has an identity by which the measuring device 7 can detect that a simulation device 1 has been connected to the measuring device 7. When the measuring device 7 detects that a simulation device 1 has been connected to the measuring device 7, the sensitivity of the measuring device 7 is set to a predetermined value, corresponding to the sensitivity of the simulation device 1. The value of the sensitivity of the simulation device 1 may be stored in the simulation device 1 or in the measuring device 7. The sensitivity expresses the relation between a certain electrical output value from the simulation device 1 and the concentration of the gas to be measured, e.g. nitrogen monoxide. The sensitivity may e.g. be expressed in nanoampere (nA)/ppm or in millivolt (mV)/ppm (ppm stands for parts per million).

The measuring device 7 may detect the identity of the simulation device 1 by the simulation device 1 sending an identification signal to the measuring device 7.

The measuring device 7 may be of a type where the gas sensor 9 is electrically disconnected from the measuring device 7 with a switch (not shown) but not removed from the measuring device 7. The electrical connector for the gas sensor 9 can in this case be called sensor connector. The simulation device 1 is in this case connected to a separate electrical connector (not shown, hereafter called simulation connector) to be in electrical connection with the measuring device 7. The simulation connector may be associated with a switch (not shown) that in one position connects the simulation connector with the measuring device 7 and in another position disconnects the simulation connector from the measuring device 7.

Alternatively, only one switch associated with both the sensor connector and the simulation connector and which alternatively electrically connects the sensor connector or the simulation connector to the measuring device 7 may be used.

After the simulation device 1 has been connected to the measuring device 7, the measuring device 7 is reconnected to the power supply and it is checked that the indicator 14 lights up as the power supply is connected to the measuring device 7. The simulation device 1 may contain means giving a signal to the measuring device 7 that a simulation device is connected to the measuring device 7. Alternatively, the simulation device 1 may receive a signal from the measuring device 7 which is sent by the measuring device 7 to detect that a simulation device is connected to the measuring device 7 and not a gas sensor 9.

The measuring device 7 may also contain means to signal or indicate that a simulation device is connected to the measuring device 7.

For one type of measuring device 7 (one model of the NIOX MINO®) the following steps are carried out to bring the measuring device 7 to a state of being ready to receive the simulation signal (simulation signal ready state) from the simulation device 1;

First it is checked that the indicator 14 is not lit. Then a human empties hers/his lungs, then inhales deeply to total lung capacity through the gas inlet opening 70 of the measuring device. Then the human exhales slowly through the gas inlet opening 70 of the measuring device.

Within a certain period of time, e.g. 5 seconds, after completion of the exhalation the start button 13 is pressed to feed the simulation signal to the measuring device 7. When the start button 13 is pressed, the indicator 14 lights up to indicate that the simulation device 1 is active and the simulation signal is fed to the measuring device 7.

The simulation device 1 may also be used with measuring devices 7 with other ways of bringing the measuring device 7 to a simulation signal ready state. Examples of such other ways are to connect the simulation device 1 to the measuring device 7 or to give a command to the measuring device 7 via some sort of interface.

After the simulation signal has been fed to the measuring device 7, instantly or after a certain time, the measuring device 7 displays a measured value or a reading corresponding to the simulation signal.

Now the reading or the displayed value of the measuring device 7 is noted or recorded and compared with, and/or evaluated in relation to, the value or level of the simulation signal i.e. the setting of the selection device 12. If the selection device 12 is set to the level 15 ppb the measuring function of the measuring device is considered satisfactory if the displayed value is within a certain interval around 15 ppb, e.g. 10-20 ppb or 12-18 ppb, depending on the specification for the particular measuring device 7 in question. Hence, the reading or the displayed value of the measuring device 7 is evaluated in relation to the known value or level of the simulation signal.

The above described procedure is then repeated for the other levels of the simulation signal that should be tested, e.g. 75 ppb.

The simulation device 1 may have different types of selection devices, e.g. a slide switch, a rotary switch, a touch screen or any other type of switch with the possibility of selecting at least one signal level. Moreover, the simulation device 1 can receive a selection signal for selecting the signal level via the electrical connector connecting the simulation device 1 with the measuring device 7.

Instead of a fixed scale or graduation the simulation device 1 can have a screen or display presenting the level set for the simulation signal.

The signal levels possible to select on the simulation device 1 and the number of levels that can be selected can of course be freely chosen. For example dependent on the type of output signal generated by the gas sensor 9 in question, or on a certain application.

It is conceivable with gas sensors that generate several output signals. Therefore, in another preferred embodiment of the simulation device 1, the simulation device 1 generates several simulation signals. The signal levels of these simulation signals may be set individually with separate selection devices for each signal or there can be predetermined combinations of signal levels for the different simulation signals where each combination can be selected with just one selection device. Otherwise the functioning of a simulation device 1 according to this embodiment is in principle the same as described above. In the case that the simulation device 1 generates several simulation signals the selection signal, mentioned previously, can be used both to select a particular simulation signal and to set its signal level.

The simulation device 1 can also be controlled via some sort of user interface preferably in connection with software, the user interface and software being comprised in the measuring device 7 and/or in the simulation device 1. Functions like the selection device 12, the start button 13 and the indicator 14 can then be implemented in software and be controlled or executed via the user interface. If the measuring device 7 comprises the user interface, the commands sent via the user interface to the simulation device 1 may be sent via the electrical connector 16. The simulation device 1 may also be equipped with other forms of interfaces, in addition to, or instead of, the electrical connector 16. Such interfaces may be wired, wireless, optical or of any other suitable type. In the case referred to in the previous sentence, if the measuring device 7 comprises the user interface, the commands sent via the user interface to the simulation device 1 can then be sent via a corresponding, e.g. wired, wireless or optical, communication interface of the measuring device 7 or an accessorial communication interface.

The user interface can for example be a display, screen, touch screen, mouse pad or a keypad or a combination thereof.

Zero Level Checking

Figure 1A:
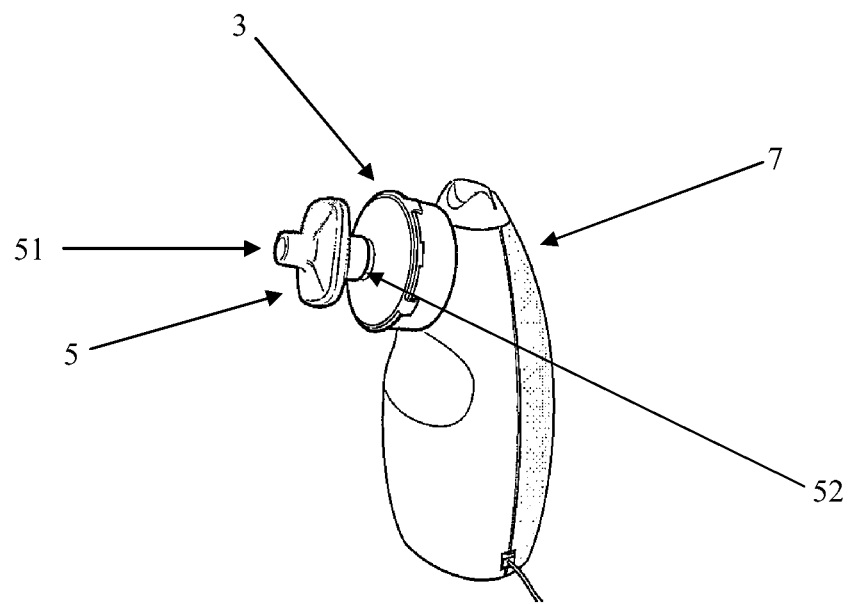
FIGS. 1A and 1B show one example of a measuring device 7 with a scrubber or filter 3 and an input filter 5.
Figure 1B:
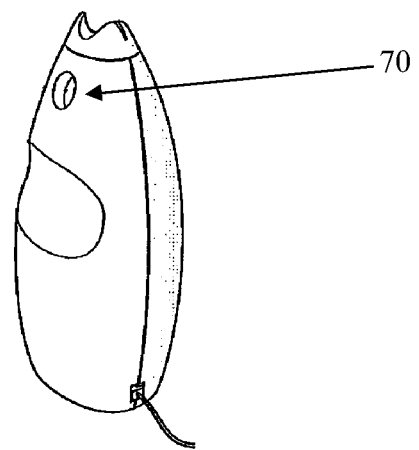
Figure 5:
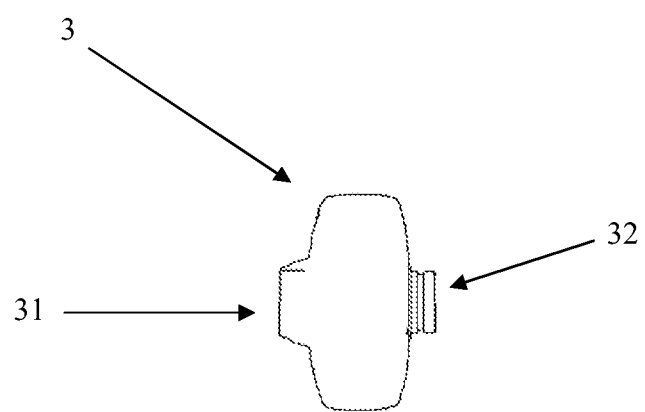
FIG. 5 shows another embodiment of a scrubber or filter 3 used in the method according to the invention.

In the description below it will be referred to FIGS. 1, 2 and 5. By way of example FIG. 1A shows a scrubber or filter 3 that is connected with its output connection end 32 to a gas inlet opening 70 of the measuring device 7, and an input filter 5 that is connected with its output connection end 52 to an input connection end 31 of the scrubber or filter 3.

In a further preferred embodiment of the method according to the invention is, preferably in addition to the use of the simulation device 1, a scrubber or filter 3, for example a NO-scrubber, used to test the measuring function of the measuring device 7. The measuring device 7 can be of a type for diagnostic gas measurements, for example for measuring the concentration of nitrogen monoxide in exhaled breath.

The scrubber or filter 3 substantially removes a certain gas from a gas mixture that passes through the scrubber or filter. For example, when a gas containing nitrogen monoxide is supplied to an input connection end of a NO-scrubber, the gas leaving an output connection end of the NO-scrubber is substantially free from nitrogen monoxide.

Different measuring devices 7 may have different thresholds or baselines for the highest concentration of a gas, e.g. nitrogen monoxide, which is still interpreted as a zero concentration. Therefore, the requirements on the rest concentration of the gas to be measured, e.g. nitrogen monoxide, at the output of the scrubber or filter 3 depend on the measuring device 7. An example of a suitable NO-scrubber or NO-filter is the NIOX MINO® QC Filter, under development by Aerocrine AB, Solna, Sweden. This NO-scrubber or NO-filter has a rest concentration of nitrogen monoxide below 5 ppb. When used for measuring nitrogen monoxide, one model of the measuring device NIOX MINO® indicates a concentration of nitrogen monoxide below 5 ppb as a zero reading.

In this part of the method according to the invention a human supplies exhaled breath via a scrubber or filter 3 to the gas inlet opening 70 of the measuring device 7. The scrubber or filter 3 has a maximum rest concentration at the output thereof that is below or equals the threshold or baseline of the measuring device 7 for a zero reading for the gas to be measured. Hence, the measuring device 7 is supplied with exhaled breath with a substantially zero concentration of the gas to be measured. It is thus verified that the measuring device 7 gives a reading within the tolerance for a zero reading. It may be the case that the measuring device 7 gives a reading or displays a measured value that is zero as long as the concentration measured or sensed by the measuring device 7 is below or equals the threshold or baseline for a zero reading for the gas to be measured.

For one type of measuring device 7 (one model of the NIOX MINO®) the measuring device 7 has an additional gas inlet opening 71 and the following is performed; the output connection end 32 of a scrubber or filter 3 is connected to the gas inlet opening 70 on the measuring device 7, a human then empties hers/his lungs, inhales deeply through the input connection end 31 of the scrubber or filter 3, and hence via the additional gas inlet opening 71, to total lung capacity, and then slowly exhales through the input connection end 31 of the scrubber or filter 3.

Figure 2A:
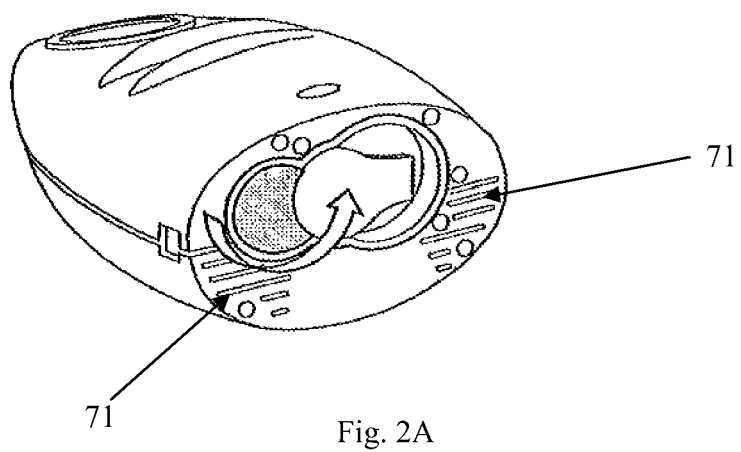
FIGS. 2A-2C show the bottom of the measuring device 7.
Figure 2B:
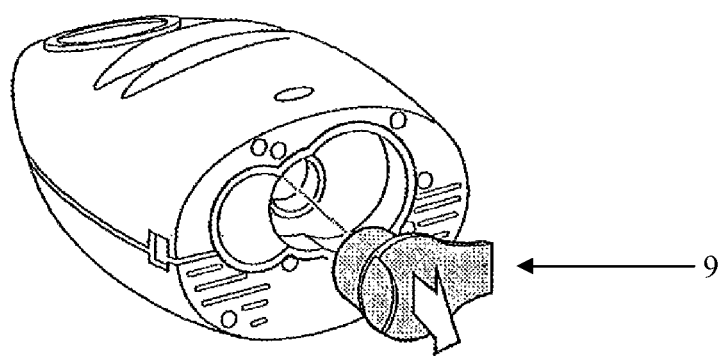
Figure 2C:
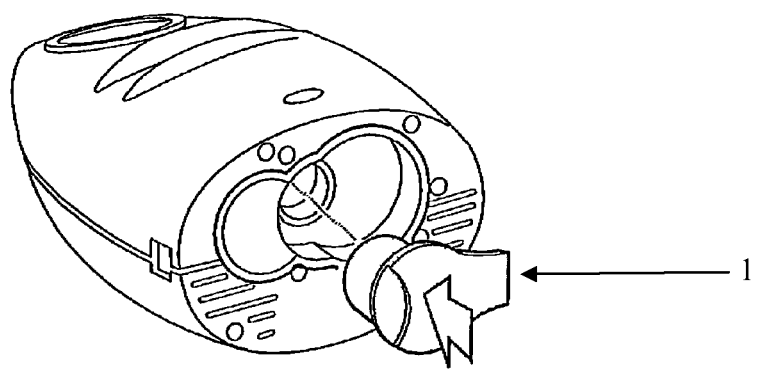

In this type of measuring device 7 the gas inlet opening 70 hence also functions as a gas outlet opening during the human inhalation. The additional gas inlet opening 71 is shown in FIG. 2A.

Hence, the measuring device 7 is supplied with exhaled breath substantially free from the gas to be measured, for example nitrogen monoxide.

There are of course other possibilities of supplying exhaled breath to the input connection end 31 of the first scrubber or filter 3. For example human exhalation through the input connection end 31 of the scrubber or filter 3 without other preceding steps, or supplying exhaled breath to the input connection end 31 of the scrubber or filter 3 from a reservoir, just to mention some examples.

Now the reading or the displayed measurement value of the measuring device 7 is noted or recorded and compared with, and/or evaluated in relation to, the expected reading. The expected reading is one below the threshold value or baseline for a zero concentration for the measuring device in question. The specific conditions to be met for the test to be satisfactory are different for different measuring devices 7.

Human Exhalation

In the description below it will be referred to FIGS. 1 and 2.

In a further preferred embodiment of the method according to the invention is, preferably in addition to the use of the simulation device, human exhalation used. The measuring device 7 can be of a type for diagnostic gas measurements, for example for measuring the concentration of nitrogen monoxide in exhaled breath.

For gases that can be present in exhaled breath often the interval or at least the approximate interval for the concentration of a certain gas is known, and this knowledge is used in this part of the invention to test the measuring function of the measuring device 7.

In this part of the method according to the invention a human supplies exhaled breath to the inlet opening 70 of the measuring device 7. It is verified that the measuring device 7 gives a reading within the interval for the concentration in exhaled breath of the gas to be measured.

Preferably the human supplies exhaled breath to the measuring device 7 through an input filter 5 capable of removing or filtering out moist, virus, microbes and bacteria and the like from the gas, e.g. exhaled breath that passes the filter. An example of a suitable filter is the NIOX® PATIENT FILTER, under development by Aerocrine AB, Solna, Sweden.

For one type of measuring device 7 (one model of the NIOX MINO®) the measuring device 7 has an additional gas inlet opening 71 and the following is performed; an input filter 5 is connected with its output connection end 52 to the gas inlet opening 70 of the measuring device 7. A human then empties hers/his lungs. Then the human inhales deeply through the input connection end 51 of the input filter 5, and hence via the additional gas inlet opening 71, to total lung capacity. The human then slowly exhales through the input connection end 51 of the input filter 5. In this type of measuring device 7 the gas inlet opening 70 hence also functions as a gas outlet opening during the human inhalation. The additional gas inlet opening 71 is shown in FIG. 2A.

Now the reading or the displayed value of the measuring device 7 is noted or recorded and compared with, and/or evaluated in relation to, the expected reading. For example, the concentration of nitrogen monoxide in exhaled breath may be in the interval of 5-300 ppb, but normally is in the interval of 5-30 ppb for a healthy human.

In another preferred embodiment the human inhales gas substantially free from, or with a reduced concentration of, the gas to be measured before supplying exhaled breath to the measuring device 7. This is an advantage in the case when the gas to be measured is present also in the ambient air. If the gas to be measured is present in the ambient air this can influence the concentration of the gas to be measured in the exhaled breath of the human. But by letting the human inhale a gas substantially free from, or with a reduced concentration of, the gas to be measured the influence of such a gas presence can be eliminated or at least almost eliminated, or reduced.

There are several possible ways in which a human could inhale gas substantially free from, or with a reduced concentration of, the gas to be measured. One way is by inhaling through a separate device incorporating a suitable inhalation scrubber or inhalation filter and then supplying exhaled breath to the measuring device 7.

The measuring device 7 could also comprise such an inhalation scrubber or inhalation filter connected to an additional gas inlet opening 71, and means allowing a human to inhale air via the additional gas inlet opening 71 and the thereto connected inhalation scrubber or inhalation filter. The human could also inhale gas substantially free from, or with a reduced concentration of, the gas to be measured, from a gas holder.

Such an inhalation scrubber or inhalation filter can substantially completely remove the gas to be measured from the gas mixture that passes the inhalation scrubber or inhalation filter, but it can also reduce the concentration of the gas to be measured in the gas mixture that passes the inhalation scrubber or inhalation filter to a variable degree. The degree of reduction depends on the requirements in each case.

The input filter 5 can of course also be used together with the scrubber or filter 3 connected to the gas input opening 70. The input filter 5 is then connected with its output connection end 52 to the input connection end 31 of the scrubber or filter 3 and exhaled breath is supplied to the input connection end 51 of the input filter 5.

Although the method and the device according to the invention have been exemplified with some examples relating to the measurement of the concentration of nitrogen monoxide in exhaled breath, of course other applications are possible. The method and the device according to the invention are for example equally well suited when it comes to applications relating to the measurement of other gases in exhaled breath, in air or in other gas mixtures. Examples of such other gases are ethanol, acetone, carbon dioxide, carbon monoxide, oxygen, hydrogen, or nitrogen dioxide. The method and the device according to the invention are also applicable to measuring devices measuring other parameters of a gas than the concentration.

The scrubber or filter of course has to be chosen in relation to the gas to be measured.

Consequently, the invention is not restricted to the described embodiments, but may be varied freely within the scope of the appended claims.

The invention claimed is:

1. A method for testing a measuring function of a measuring device for measuring nitrogen monoxide in a sample of exhaled breath, the measuring device including a first part having a gas sensor for measuring nitrogen monoxide that generates at least one output signal and a second part that processes and evaluates the output signal, the method comprising:

receiving exhaled breath at the gas sensor by way of a scrubber or filter that substantially removes nitrogen monoxide from the exhaled breath so that the exhaled breath at the gas sensor contains no more than a known rest concentration of nitrogen monoxide, the rest concentration being greater than a zero concentration of nitrogen monoxide and being a concentration threshold up to which the measuring device is to produce a zero reading for the concentration of nitrogen monoxide in the exhaled breath;

processing the exhaled breath in the first part to generate the output signal from the gas sensor, the output signal indicating a measured concentration of nitrogen monoxide in the exhaled breath received at the gas sensor; and evaluating the output signal with the second part to establish an evaluation value of the concentration of nitrogen monoxide in the exhaled breath and confirming that the evaluation value is zero to verify that the measuring device gives a zero reading when nitrogen monoxide in the exhaled breath at the gas sensor is within a tolerance for generating the zero reading.

2. The method according to claim 1, further comprising;
a. connecting at least one simulation signal with a known signal value to the second part of the measuring device; and
b. evaluating the reading of the second part of the measuring device in relation to the known signal value of the at least one simulation signal.

3. The method according to claim 2, further comprising;
a. disconnecting the first part from the measuring device; and
b. connecting a simulation device, generating the at least one simulation signal, to the measuring device.

4. The method according to claim 2, further comprising; setting the at least one simulation signal of the simulation device to at least one of a plurality of signal levels.

5. The method according to claim 1, further comprising;
a. connecting an input filter, for filtering out moist, virus, moisture, viruses, microbes, and bacteria, having an input and an output connection end, with its output connection end to a gas inlet opening of the measuring device; and
b. receiving the exhaled breath at the input connection end of the input filter.

6. The method according to claim 1, further comprising;
a. filtering air that is inhaled so as to be substantially free from, or with a reduced concentration of, the nitrogen monoxide to be measured, the filtered and inhaled air being exhaled as the received breath.

7. A simulation device for use in the method according to claim 3, the simulation device for connection to the measuring device for nitrogen monoxide measurements in exhaled breath when testing the measuring function of the measuring device, the simulation device comprising generating means for generating at least one simulation signal simulating at least one output signal of a gas sensor for the measuring device, wherein the at least one simulation signal can attain at least one signal level, and wherein a certain signal value corresponds to a certain concentration of nitrogen monoxide, the simulation device having a specific sensitivity, and wherein the simulation device has an identity detectable by the measuring device, enabling the sensitivity of the measuring device to be set to the sensitivity of the simulation device.

8. The simulation device according to claim 7, further comprising;
selection means for selecting at least one signal level of the at least one simulation signal.

9. The method according to claim 2, further comprising;
a. generating at least one simulation signal simulating the at least one output signal from the gas sensor, where the at least one simulation signal can attain at least one signal level; and
b. feeding the at least one simulation signal to the second part of the measuring device.

10. The simulation device according to claim 8, wherein the selection means is selected from the group consisting of a switch, a touch screen, and a connector for receiving an external signal.

11. The method according to claim 1, wherein the scrubber or filter has input and output connection ends, and the method further comprises connecting the output connection end of the scrubber or filter to a gas inlet opening of the measuring device.

* * * * *

UNITED STATES PATENT AND TRADEMARK OFFICE
CERTIFICATE OF CORRECTION

PATENT NO.         : 8,539,809 B2                                              Page 1 of 1
APPLICATION NO. : 12/525301
DATED              : September 24, 2013
INVENTOR(S)        : Hemmingsson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 776 days.

Signed and Sealed this

Fifteenth Day of September, 2015

Michelle K. Lee
*Director of the United States Patent and Trademark Office*